Nov. 9, 1954
R. G. JELLY
Plant Pat. 1,316
ROSE PLANT
Filed Oct. 26, 1953
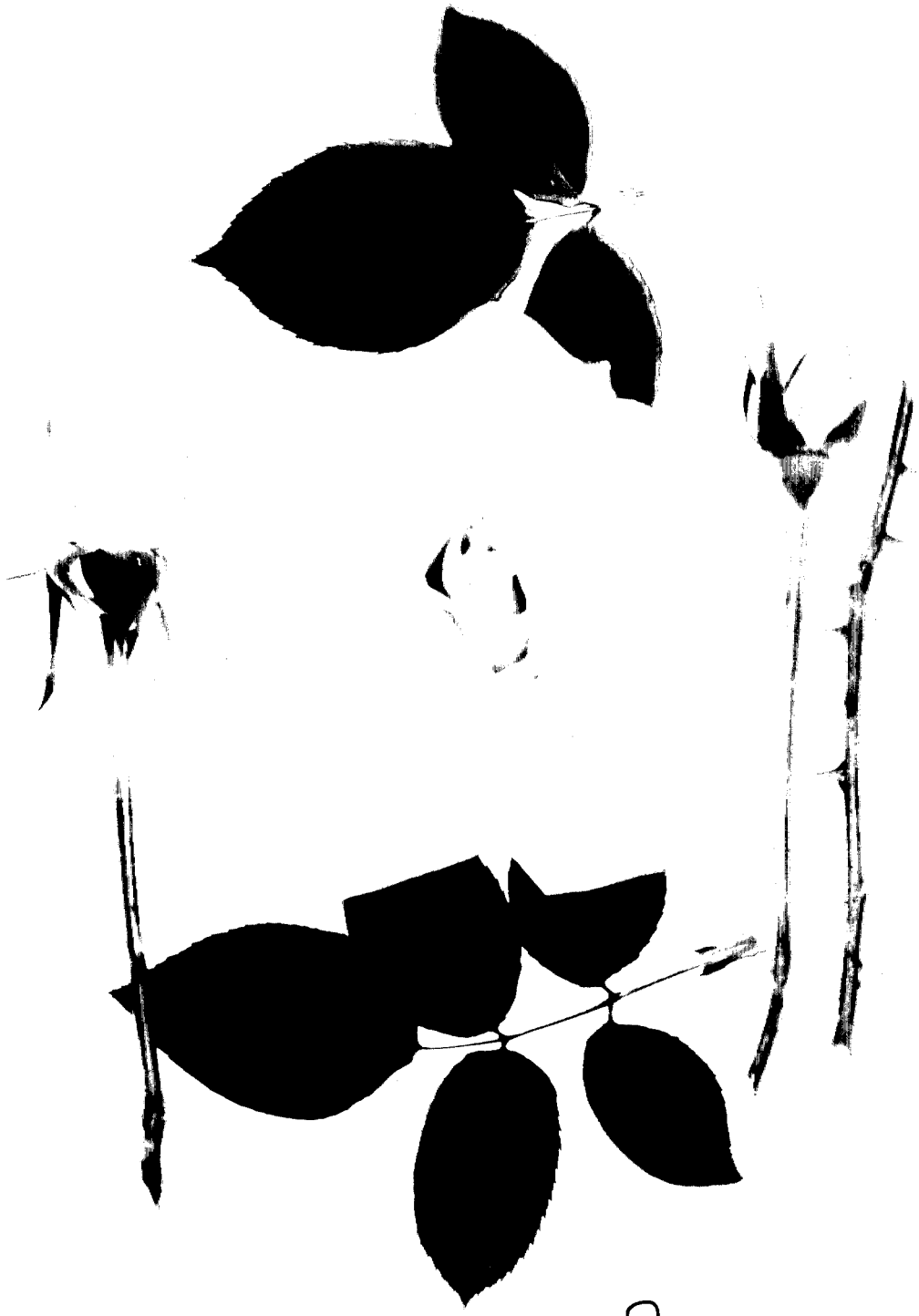
Inventor
R. G. Jelly
By: Cobb & Cobb
Attorneys United States Patent Office Plant Pat. 1,316
Patented Nov. 9, 1954

1,316

ROSE PLANT

Robert G. Jelly, Richmond, Ind., assignor to E. G. Hill Co., Inc., Richmond, Ind., a corporation of Indiana Application October 26, 1953, Serial No. 388,468

1 Claim. (Cl. 47—61)

The present invention relates to a new and distinct variety of rose plant of the hybrid tea class which was originated by me by crossing two unnamed and unpatented seedlings of unknown origin.

The primary objective of this breeding was to create a new productive pink rose that is suitable for forcing under commercial greenhouse conditions. This objective was fully achieved, and my new variety is additionally characterized by its strikingly erect habit of growth, by its relatively long-pointed, large and perfectly formed buds which open into a high-centered, well-formed flower of a distinctive pink general color tonality, and by the superior keeping quality of its blooms.

The foregoing characteristics definitely distinguish my new variety from its parents, as well as from all other varieties of its class, and represent a unique combination of characteristics never attained heretofore, so far as I am aware.

Asexual reproduction of my new variety by grafting at Richmond, Indiana, and by budding at San Leandro, California, shows that the foregoing characteristics and distinctions come true to form and are established and transmitted through succeeding propagations.

The accompanying drawing shows typical specimens of the flowers, foliage and stems of my new variety in different stages of development and depicted in color as nearly true as it is reasonably possible to make the same in a color illustration of this character.

The following is a detailed description of my new variety, with color terminology in accordance with Ridgways' Color Standards and Nomenclature:

Type: Bush; greenhouse; seedling; for cut-flower production.

Class: Hybrid tea.

Breeding: Seedling.

*Seed parent.*—An unnamed seedling of unknown parentage.

*Pollen parent.*—An unnamed seedling of unknown parentage.

Propagation: Holds its distinguishing characteristics through succeeding propagations by both grafting and budding.

*Flower*

Locality where grown and observed: Richmond, Indiana.

Flowers borne: 1 to stem; on moderately strong stems of medium length.

Quantity of bloom: Free, in greenhouse.

Continuity: Continuous.

Fragrance: Spicy.

Bud:

*Peduncle.*—Medium length; medium diameter; erect; medium strong; almost smooth; no thorns or hairs, but with few prickles of Straw Yellow, Plate XVI, color. Color—Biscay Green, Plate XVII, shading to Saccardo's Olive, Plate XVI.

*Before calyx breaks.*—Size—medium. Form—short-pointed; with a conspicuous neck; with occasional foliaceous appendages on the surface of the bud; with foliaceous parts extending beyond the tip of the bud equal to ¾ or more of its length. Color—Cress Green, Plate XXXI.

*As calyx breaks.*—Color—Rose Doree, Plate I at the petal margin, shading to Pale Lemon Yellow, Plate IV at base, with intermediate or basic color Bittersweet Pink, Plate II.

*As first petal opens.*—Size—medium-large. Form—long-pointed. Color: outside—Rose Doree, Plate I at the petal margin, shading to Pale Lemon Yellow, Plate IV at base, with intermediate or basic color Bittersweet Pink, Plate II; inside—Rose Doree, Plate I at petal margin, shading to Pale Lemon Yellow, Plate IV at base, with intermediate or basic color Bittersweet Pink, Plate II.

*Opening.*—Opens up well in greenhouse; is not affected by hot weather except for normal reduction of flower size.

Bloom:

*Size (when fully open).*—Large; from 5 to 6 inches.

*Petalage.*—Double; from 28 to 36 petals; arranged regularly.

*Form.*—High-centered at first; becoming very high-centered; petals being at first tightly and slightly rolled outward, but becoming only slightly rolled outward at maturity.

Petals: Moderately thick; leathery; with both inside and outside satiny.

*Shape.*—Outside—ovate; apex slightly mucronate, with 1 to several notches. Intermediate—slightly ovate, with apex slightly obtuse to flat. Inner—round; apex mucronate, with 1 notch (cleft).

This description of a newly opened flower was made from a rose grown in a greenhouse in the month of March, at Richmond, Indiana:

*Color.*—Outside petal: Outside surface—Spinel Pink, Plate XXVI; margin shading to Hermosa Pink, Plate I; with base Amber Yellow, Plate XVI. Inside surface—Hermosa Pink, Plate I, with base Primuline Yellow, Plate XVI. Intermediate petal: Outside surface—Spinel Pink, Plate XXVI; margin shading to Hermosa Pink, Plate I; with base Amber Yellow, Plate XVI. Inside surface—Hermosa Pink, Plate I, with Strontian Yellow, Plate XVI base. Inner petal: Outside surface—Begonia Rose, Plate I; margin shading to Geranium Pink, Plate I; with base Amber Yellow, Plate XVI. Inside surface—Geranium Pink, Plate I, with base Lemon Chrome, Plate IV.

This description was made from a rose that was open for three days in a greenhouse in the month of March, at Richmond, Indiana:

*Color.*—Outside petal: Outside surface—Hermosa Pink, Plate I, shading to Shrimp Pink, Plate I, with base Straw Yellow, Plate XVI. Inside surface—Shrimp Pink, Plate I, shading to Seashell Pink, Plate XIV, with base Lemon Chrome, Plate IV. Intermediate petal: Outside surface—Thulite Pink, Plate XXVI; margin shading to Hermosa Pink, Plate I; with base Massicot Yellow, Plate XVI. Inside surface—Hermosa Pink, Plate I, with base Strontian Yellow, Plate XVI. Inner petal: Outside surface—Thulite Pink, Plate XXVI, with base Strontian Yellow, Plate XVI. Inside surface—Cameo Pink, Plate XXVI, shading to Shell Pink, Plate XXVIII, with base Strontian Yellow, Plate XVI.

*General color effect.*—Newly opened flower—Spinel Pink, Plate XXVI. 3-days open—Hermosa Pink, Plate I.

*Behavior (in greenhouse).*—Persist; unaffected by hot or dry weather; fading Hermosa Pink, Plate I to Shrimp Pink, Plate I.

*Flower longevity.*—Cut flowers grown in greenhouse and kept at living-room temperatures—5 days in March.

*Plant*

Foliage:

*Leaves.*—Compound of 5 or sometimes 7 leaflets; normally abundant; medium size; moderately leathery.

*Leaflets.*—Shape—oval. Apex—acute to cuspidate. Base—obtuse. Margin—serrate. Color—Mature; upper surface—Dusky Olive Green, Plate XLII; under surface—Pea Green, Plate XLVII.

Young: upper surface—Burnt Lake, Plate XII; under surface—Acajou Red, Plate XIII. Rachis—medium. Upper side—grooved; prickly; under side—smooth. Stipules—very short; very narrow; without points; with very short globular ends turning out at an angle of 90°.

Growth (in greenhouse):

*Habit.*—Upright; branched.

*Growth.*—Moderately free.

*Canes.*—Medium diameter.

*Main stems.* — Color — Calla Green, Plate V. Thorns—Few; medium length. Color—Indian Red, Plate XXVII. Prickles—few. Color—too small to distinguish. Hairs—none.

*Branches.*—Color—dark dull Yellow Green, Plate XXXII. Thorns — several; medium length; straight; narrow. Color—Ochre Red, Plate XXVII. Prickles—several; very small. Color—too minute to distinguish. Hairs—none.

*New shoots.*—Color—Prussian Red, Plate XXVII. Thorns—several; medium length; straight; with narrow base. Color—Bordeaux, Plate XII. Prickles—few. Color—Bordeaux, Plate XII. Hairs—none.

*Reproductive organs*

Stamens: Medium number; arranged regularly; tucked in calyx.

Filaments: Medium length; with anthers. Color—Light Cadmium, Plate IV.

Anthers: Medium; all open at once. Color—Light Orange Yellow, Plate VI.

Pollen: Moderate. Color—Honey Yellow, Plate XXX.

Pistils: Many.

Styles: Uneven; medium length; medium heavy; bunched. Color—Lemon Chrome, Plate IV.

Stigma: Color—Spectrum Red, Plate I.

Ovaries: Some protruding from calyx.

Hips: Long; ovoid; with inconspicuous neck; pear-shaped; prickly; walls thick and fleshy. Color—Primuline Yellow, Plate XVI.

Sepals: Permanent; medium length; recurved.

*Color.* — Inside — Deep Chrysolite Green, Plate XXXI. Outside—Absinthe Green, Plate XXXI.

Seeds: Many; large.

I claim:

A new and distinct variety of rose plant of the hybrid tea class, substantially as herein shown and described, characterized particularly as to novelty by its very erect habit of growth, by its relatively large, long-pointed, perfectly shaped buds which open into high-centered and well-formed flowers of a distinctive pink general color tonality, by the superior keeping quality of its blooms, and by its suitability for forcing under commercial greenhouse conditions.

No references cited.